United States Patent
McNeil-Watson et al.

(10) Patent No.: US 10,006,851 B2
(45) Date of Patent: Jun. 26, 2018

(54) LIGHT SCATTERING MEASUREMENTS USING SIMULTANEOUS DETECTION

(75) Inventors: Fraser McNeil-Watson, Malvern (GB); Malcolm Connah, Malvern (GB); Robert Jack, Bromsgrove (GB); David McKnight, Coventry (GB)

(73) Assignee: Malvern Panalytical Limited, Malvern (GB)

( * ) Notice: Subject to any disclaimer, the term of this patent is extended or adjusted under 35 U.S.C. 154(b) by 0 days. days.

(21) Appl. No.: 12/321,123

(22) Filed: Jan. 15, 2009

(65) Prior Publication Data

US 2009/0251696 A1 Oct. 8, 2009

Related U.S. Application Data

(60) Provisional application No. 61/011,143, filed on Jan. 15, 2008.

(51) Int. Cl.
| | | |
|---|---|---|
| *G01N 21/00* | (2006.01) | |
| *G01N 15/14* | (2006.01) | |
| *G01N 15/00* | (2006.01) | |

(52) U.S. Cl.
CPC ..... *G01N 15/1429* (2013.01); *G01N 15/1427* (2013.01); *G01N 2015/0065* (2013.01); *G01N 2015/0096* (2013.01)

(58) Field of Classification Search
CPC ............................... G01N 21/00; G01N 15/02
USPC .......................................................... 356/336
See application file for complete search history.

(56) References Cited

U.S. PATENT DOCUMENTS

| | | | | |
|---|---|---|---|---|
| 4,710,025 A | * | 12/1987 | Wyatt | G01N 15/1436 250/574 |
| 4,830,494 A | | 5/1989 | Ishikawa | |
| 5,030,843 A | * | 7/1991 | Wakamura | G01N 15/0205 250/574 |
| 5,627,642 A | * | 5/1997 | Dhadwal | B82Y 15/00 356/336 |
| 5,633,503 A | | 5/1997 | Kosaka | |
| 5,956,139 A | * | 9/1999 | Meyer | G01N 15/0211 356/338 |
| 6,177,277 B1 | | 1/2001 | Soini | |

(Continued)

FOREIGN PATENT DOCUMENTS

| | | |
|---|---|---|
| CN | 102066901 B | 7/2013 |
| EP | 2235501 A2 | 7/2009 |

(Continued)

OTHER PUBLICATIONS

Bantchev Grigor et al: "Simple multiangle, multicorrelator depolarized dynamic light scattering apparatus," Review of Scientific Instruments, AIP, Melville, NY, vol. 77, No. 4, Apr. 4, 2006 (Apr. 4, 2006), pp. 13902-043902.

(Continued)

*Primary Examiner* — Roy M Punnoose
(74) *Attorney, Agent, or Firm* — Kristofer E. Elbing

(57) ABSTRACT

Methods and apparatus for measuring particle characteristics are disclosed. In one aspect, an amount of light arising from interaction between light and a suspended sample is detected simultaneously with the acquisition of a photon count from a different direction. At least one measure of particle characteristics can then be derived based at least in part on timing between information from the steps of acquiring and detecting.

25 Claims, 6 Drawing Sheets

(56) References Cited

U.S. PATENT DOCUMENTS

| | | | |
|---|---|---|---|
| 6,252,658 B1 * | 6/2001 | Togawa | G01N 15/0211 356/335 |
| 2007/0041877 A1 * | 2/2007 | Maurer | G01N 21/0332 422/400 |
| 2009/0122311 A1 | 5/2009 | Kanda | |
| 2012/0073972 A1 * | 3/2012 | Watson | B01L 3/5025 204/549 |

FOREIGN PATENT DOCUMENTS

| | | |
|---|---|---|
| JP | 2003315243 | 11/2003 |
| JP | 2006138727 | 6/2006 |
| JP | 5259736 B2 | 5/2013 |
| WO | WO1996/022521 | 7/1996 |
| WO | WO2007018087 | 2/2007 |
| WO | WO2008/092272 | 8/2008 |

OTHER PUBLICATIONS

Aberle L B et al: "Effective Suppression of Multiply Scattered Light in Static and Dynamic Light Scattering," Applied Optics, Optical Society of America, Washington, DC, vol. 37, No. 27, Sep. 20, 1998 (Sep. 20, 1998), pp. 6511-6524.

* cited by examiner

LIGHT SCATTERING MEASUREMENTS USING SIMULTANEOUS DETECTION

CROSS-REFERENCE TO RELATED APPLICATION

This application claims the benefit of U.S. Provisional Application No. 61/011,143, filed Jan. 15, 2008, which is herein incorporated by reference.

FIELD OF THE INVENTION

This invention pertains to the measurement of particle characteristics, including dynamic measurement of very small particles.

BACKGROUND OF THE INVENTION

It is well known on both practical and theoretical grounds that the intensity of light scattered by particles smaller than the wavelength of light is a strong function of particle size. In the Rayleigh Scattering limit where particle radius is below 0.1× wavelength of illumination, the scattered intensity is proportional to particle radius raised to the sixth power and is substantially independent of scattering angle. Above this limit, the angular dependence becomes significant. To describe the scattering in this area, the optical properties of the particle are needed and particle shape also becomes important. The mathematical treatment due to Gustave Mie can be used to predict the scattering from spherical particles in all these regions. A computer program due to Dave is a convenient tool to calculate these effects, and is available as an Appendix to Bohren, C. F. and Huffman, D.R., "Absorption and Scattering of Light by Small Particles", Wiley, New York, 1983. FIG. 1 shows the scattering of light of 633 nm wavelength from particles from 10 nm to 10 microns of refractive index 1.6 and negligible absorbance (from Bohren & Huffman, supra). It is easy to see that for sizes below 100 nm the scattering angle is relatively unimportant whereas for larger sizes the scattering pattern varies, with the variation being greater at the larger scattering angle.

A computer program that can be used to calculate the scattering for spheres of particular size and refractive index is included as an appendix to Bohren, C. F. and Huffman, D. R., "Absorption and Scattering of Light by Small Particles", Wiley, New York, 1983. This paper is based on earlier work by J. V. Dave published in 1968. The documents referenced above are all herein incorporated by reference.

Note that at around 1 micron the forward-back scatter ratio is about $10^4$. Hence a light scattering measurement on a sample containing small primary particles and also larger species is very sensitive to small numbers of large particles, or even individual large particles. These unwanted contaminants may be found in all kinds of systems; they may be aggregates of the primary particle or some other material. In the study of virus particles multiplied in a growth medium, for example, whole biological cells or fragments are often present. In light scattering of flowing samples such as the efflux from a size exclusion chromatography system, particle debris from the column itself may be mixed with the molecular species of interest.

The use of simultaneous multiple detectors to analyze the intensity distribution of light scattering from a population of particles has been widely used and is known as Static Light Scattering' (SLS); when conducted using a planar array of detectors in the focal plane of a lens or equivalent optical system so that the light that is detected is in a forward direction over a limited angular range the term 'laser diffraction' is often applied. Hybrid systems combining forward, side, and backscatter, such as the Mastersizer 2000, are available, for example, from Malvern Instruments of Malvern UK.

SUMMARY OF THE INVENTION

Several aspects of this invention are presented in this specification and its claims. In one general aspect, a detection scheme using two or more photon-counting detectors, or at least one photon counting and one analogue detector, simultaneously in a dynamic light scattering experiment is described. This scheme is intended to facilitate the measurement of particle size of nanoparticles, biomolecules, viruses and similar materials in the presence of unavoidable larger sized contaminants, dust and aggregates. A similar scheme applied to static light scattering is also described.

The approach described here is expected to be of particular value in analyzing flowing samples in a chromatography experiment or other semi-continuous process. One major difficulty in applying light scattering to the eluent of a chromatography experiment is that the separation column tends to release or 'shed' particles from the column matrix. These particles are much larger than the chromatographic sample and are likely to degrade the measurement. The proposed scheme is intended to address this difficulty.

The invention may be particularly useful in the characterization by size and mass of biomolecules, cells and viruses. The detection of protein aggregates has become an important issue as their presence has a large effect on therapeutic uses of protein based drugs. Systems according to the invention should also enable improved quantitation of the proportion of aggregates and allow more precise measurement on the base protein. Measurement of virus particles by light scattering is often hampered by the presence of trash in the growth media. Similarly samples of small cells such as lymphocytes are often accompanied by a few larger cells or other material whose light scattering swamps the signal from the target cells.

Another area of application is to the study of nano-particle dispersions, which often contain large aggregates; gating out the detection of these can lead to an improved measurement of the primary particle.

In another general aspect, the invention features a particle measurement instrument that includes a light source having an output beam path, a sample cell positioned in the output beam path of the light source, and at least one photon-counting detector positioned outside of the beam path to acquire light scattered along a first scattering angle. A supplemental detector positioned outside of the beam path to acquire light scattered along a second scattering angle, different from the first, and simultaneous detection logic that is responsive to both the photon-counting detector and the supplemental detector. The simultaneous detection logic has a particle characteristics measurement output and inter-detector timing logic operative to derive the particle characteristics measurement output based at least in part on the timing between information from the photon-counting detector and information from the supplemental detector.

In preferred embodiments the photon-counting detector can be located on the same side of the sample cell as the light source outside of the beam path to acquire backward scattered light, with the supplemental detector being positioned opposite the light source from the sample cell to acquire forward scattered light. The supplemental detector can also be a photon-counting detector. The light source can be a coherent visible light source. The light source can be a narrowband visible light source. The simultaneous detection logic can include dynamic light scattering detection logic. The simultaneous detection logic can operate in real time to allow information from the supplemental detector to gate information from the photon-counting detector. The simultaneous detection logic can post-process acquired data from the photon-counting detector and acquired data from the supplemental detector after acquisition of the data from the photon-counting detector and the supplemental detector. The simultaneous detection logic can include digital signal processing logic. The simultaneous detection logic can be interactive. The simultaneous detection logic can be operative to determine the size of particles in the presence of larger contaminant particles. The simultaneous detection logic can be operative to determine relative quantities of particles in the presence of larger contaminant particles. The supplemental detector can be positioned from about 5-30 degrees off of an optical axis of the light source. The supplemental detector can be positioned from about 30-90 degrees off of an optical axis of the light source. The photon-counting detector can be positioned about 7 degrees off of an optical axis of the light source. The instrument can further include a second photon-counting detector, with the simultaneous detector being further responsive to the second photon-counting detector. The second photon-counting detector can be placed at about 90 degrees off of an optical axis of the light source at the sample cell. The instrument can have a range of particle detection that covers particles that are smaller than 100 nm in diameter. The instrument can have a range of particle detection that covers particles that are smaller than 10 nm in diameter. The simultaneous detection logic can include cross-correlation logic operative to derive the particle characteristics measurement output based at least in part on a cross-correlation between information from the photon-counting detector and information from the supplemental detector. The cross-correlation logic can gate information from the photon-counting detector when a cross correlation between output of the photon-counting detector and the supplemental detector exceeds a predetermined threshold.

In a further general aspect, the invention features a method of measuring particle characteristics that includes shining light on a suspended sample, acquiring a photon count arising from scattering of the light by the sample, detecting an amount of light arising from interaction between the light and the sample simultaneously with the step of acquiring a photon count, wherein the step of detecting detects a least some light from a direction different than a direction from which the photon count is acquired, and deriving at least one measure of particle characteristics based at least in part on timing between information from the step of acquiring and information from step of detecting. In preferred embodiments the step of shining light can shine light on suspended biomolecules, such as proteins.

DESCRIPTION OF AN ILLUSTRATIVE EMBODIMENT

Figure 1:
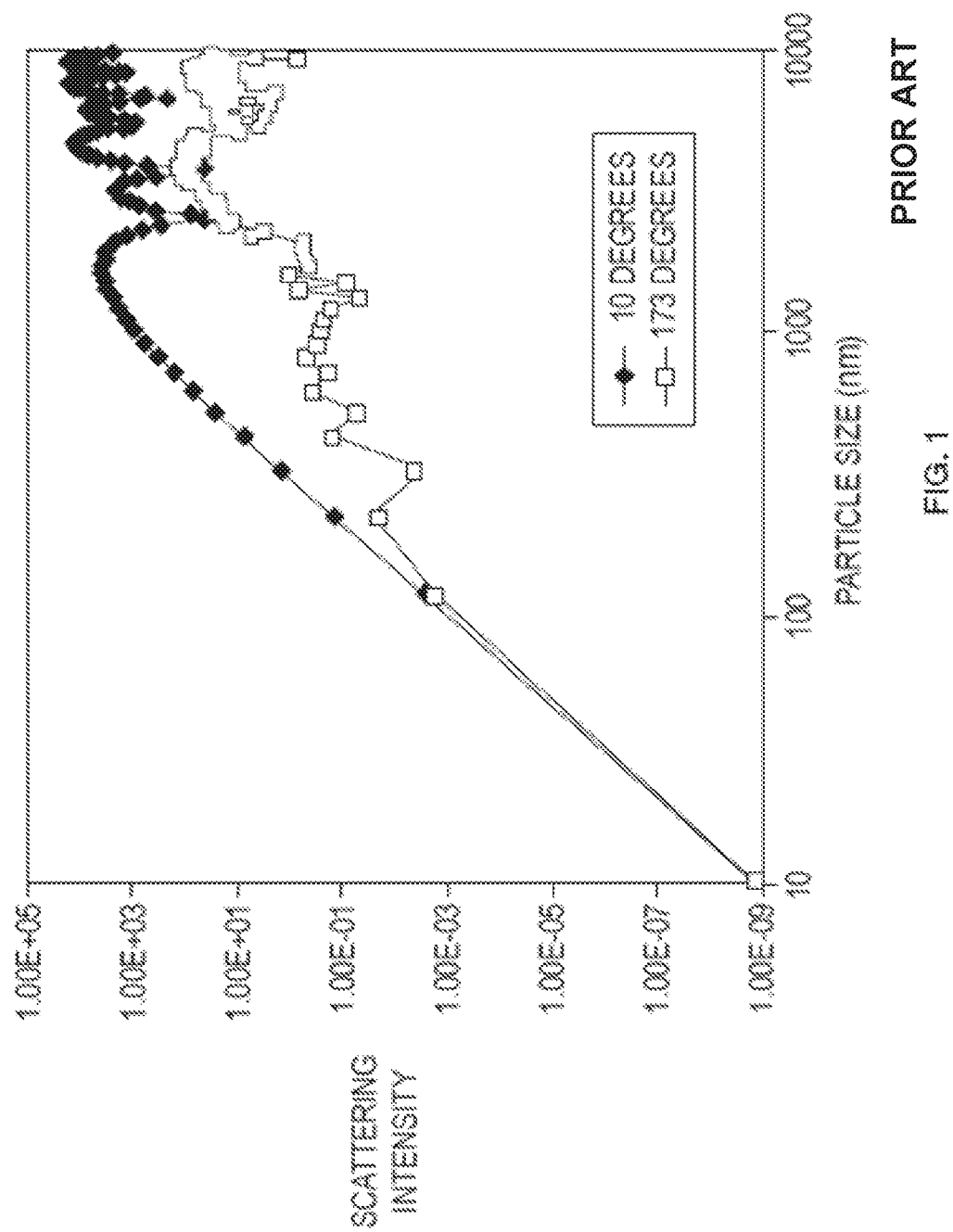
FIG. 1 is a prior art plot of scattering as a function of size and angle, from Bohren & Huffman, supra.
Figure 2:
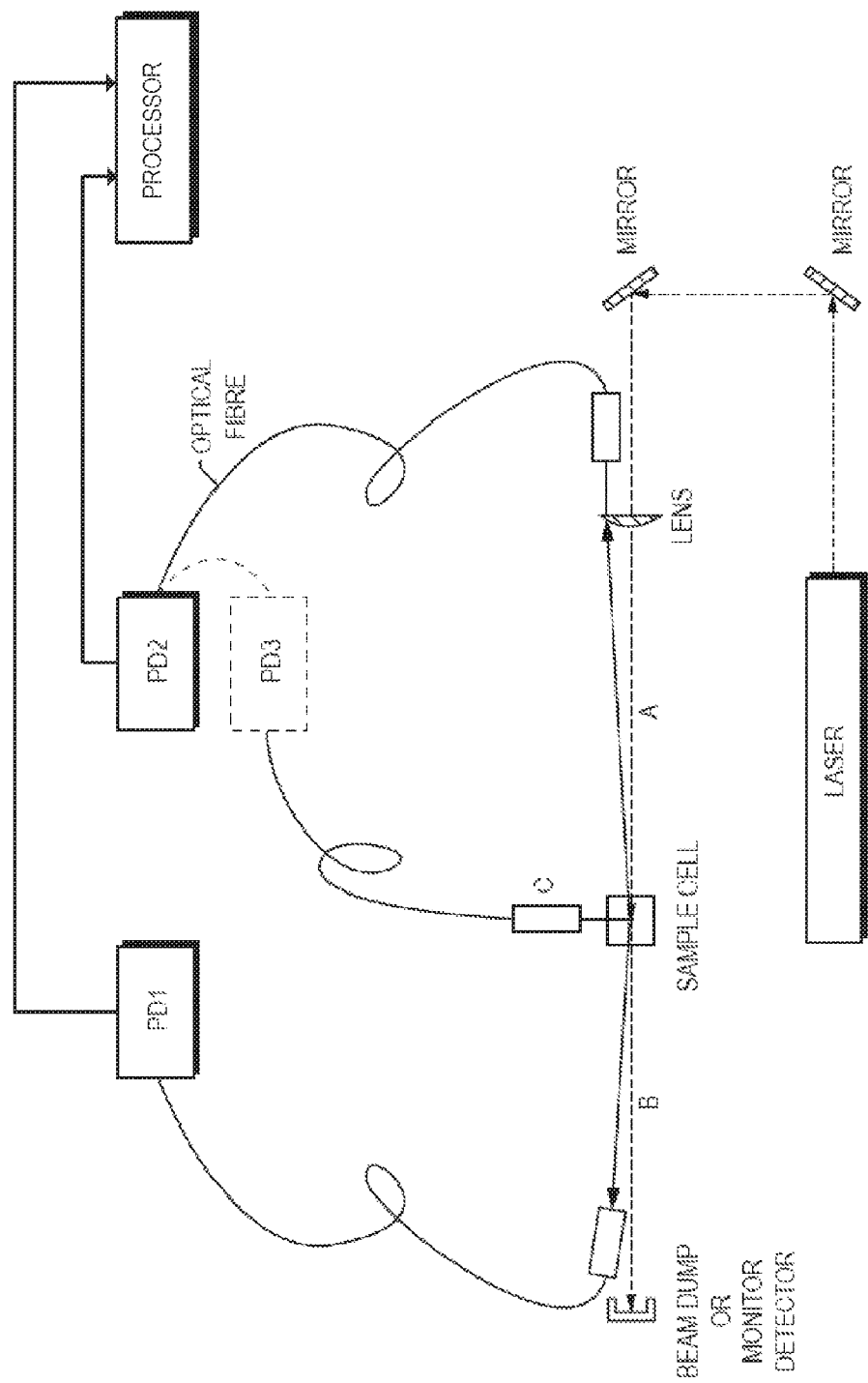
FIG. 2 is an optical block diagram of an illustrative multi-detector light scattering apparatus according to the invention.

Referring to FIG. 2, an illustrative embodiment of the invention will now be discussed in more detail. In this embodiment, a laser beam is passed through a sample cell. A photon-counting detector PD1 is preferably positioned behind the sample cell and outside of the optical path of the laser receives backscatter from the cell, such as through an optical fiber. A supplemental detector PD2, which may or may not be a photon-counting detector, is preferably positioned ahead of the sample cell and outside of the optical path of the laser, and receives forward scatter from the cell, such as through an optical fiber. One or more further optional photon-counting detectors (e.g., PD3) can be provided as well, such as to monitor sidescatter through another optical fiber. In one embodiment, PD 1 is simply switched between the PD 1 and PD2 fiber-optic pickups to acquire backscatter and sidescatter.

It is preferable to position the photon-counting detector to acquire backscattered light because it tends to receive a lower amount of signal from the aggregates in that position, but it can be positioned anywhere outside of the path of the laser beam. The supplemental detector can cover any angular range provided that it is different from, and preferably lower than, the photon-counting detector. The supplemental detector could even be implemented an integrating sphere where all angles possible were covered to give maximum sensitivity.

In one embodiment, angles shown in FIG. 2 are as follows:
Angle A 7 degrees effective detection (173 degrees—backscatter)
Angle B 5-30 degrees (typically)—forward scatter
Angle C 90 degrees—sidescatter PD1-PDN can be electronically connected to a signal processor such as a Digital Signal Processor (DSP) integrated circuit or a personal computer for post-processing. The folded optical arrangement is used on the Zetasizer Nano instrument available from Malvern instruments of Malvern, UK. The backscatter optics using the lens as shown is also used in the Zetasizer Nano and is subject to patent protection (also described as 'NIBS'—non-invasive backscatter).

The output of the supplemental detector PD2 can be used to gate one or more of the photon-counting detectors. When the output of the supplemental detector rises above a predetermined threshold, indicating that a contaminating particle is transiting the laser beam, the system disables the photon-counting detector. Photon counts can be resumed when supplemental detector levels are below the threshold. The gating can be performed in real time, or it can be performed as a post-processing operation. Other types of post-processing operations, such as digital signal processing methods, can also be applied, and these could be applied in a dedicated or interactive manner. The gating/post-processing functions can be implemented using dedicated hardware, software running on a general-purpose processor, or a combination of the two.

It should be noted that the fluctuating signals are actually resolved down to individual photon arrival times and may be sparse for low scattering samples as viewed by PD1. The signals in PD2 attain statistical significance more rapidly as forward scatter is enhanced (by the physics of scattering) and potentially by using larger acceptance angles than can be used for correlation processing by PD1.

For particles smaller than 100 nm, scattering becomes very weak and independent of angle. In this size region, as well as for larger particles smaller than 6 microns, particle size can be determined by dynamic light scattering in which fluctuations in the intensity are recorded using a photon-counting detector. These fluctuations arise from the particles undergoing Brownian motion which can be characterized by calculating a correlation function of the signal. This requires that the signal be sampled over periods much shorter than a characteristic relaxation time due to the motion and requires a fast and sensitive detector such as a photomultiplier tube (PMT) or more recently an Avalanche Photo-Diode (APD). Typical fundamental sample times are 50 nanoseconds to measure the contribution of the smallest species which may be as little as 0.6 nm diameter in a modern instrument such as the Malvern Zetasizer Nano. The signal fluctuations are recorded for example for 8 successive samples then added in pairs and recorded for 8 more 'channels' at a sample time of 50 ns, then 8 more at 100 ns and so on over 24 stages so that the final sampling time is more than 0.4 seconds. This so-called logarithmic correlation process enables a wide dynamic range in size to be characterized.

The troublesome scattering from large contaminants will be entrained in the signal and cannot readily be removed when this has happened as the correlation process usually uses every sample recorded. A typical count rate from a dispersion of 10 nm particles measured in backscatter at 173 degrees may be around $10^5$ counts per second, or 1 every ten microseconds. Most sample times at a fundamental of 50 ns and the summed versions in the first 8 sections of the correlator will be empty in most cases and many millions of samples are summed in order to recover the signal. A single dust particle of 1 micron may scatter around 15 times as much, and an aggregate or contaminant of 100 nm sizes 150 times as much; even these increases in count rate are not sufficient to enable the signal to be filtered by inspection of the immediate data. The relaxation (coherence) time for 10 nm particles diffusing in water at 25 degrees centigrade is 29.3 microseconds (assuming an illuminating wavelength of 633 nm and a scattering angle of 173 degrees). It is usual to calculate the correlation over at least 10 coherence times so the data could be collected in batches of say 300 microseconds. In this time one would expect to detect 30 photons. The accuracy of this is limited by Poissonian counting statistics to—i.e. 20%. Since 3× standard deviation fluctuations are to be expected in around 16% of cases for a pure sample we would significantly degrade the efficiency of data collection by excluding a batch of data that gave more than say 45 photons on the grounds that a dust particle might be present.

A single 1 micron particle, of similar optical properties to the 10 run population, contributes an effective count rate of 2.7 k cps, so in the 300 microsecond period only 0.81 photons may be expected. However the scattering from that same single particle at 12 degrees is around 720 times more intense; hence around 600 photons could be expected assuming a similar optical efficiency and detector sensitivity.

A threshold can then be set based on the detected light intensity, since the smaller particles will still contribute 30 photons on average in the period. A threshold of (say) 100 photons can be set. When this is exceeded, one can exclude the batch of photons collected at 173 degrees from the correlation process. A more sophisticated process could store all the photon arrival information at both angles and process the back scatter data during any period of arbitrary length when the forward angle data indicated dust is absent. In this way fixed length batches of data could be avoided and the correlation process made more efficient.

The ideal filtering method will depend on the exact experimental arrangement; in a flowing system the residence time of a dust particle will primarily depend on the flow rate. A typical volume flow in a dynamic light scattering measurement from an SEC column is around 0.5 ml/min. In a typical flow cell of cross section 2×2 mm the linear flow rate will be 2 mm/sec. Since the laser beam has a diameter of around 50 microns the residence time of any single particle is 25 ms; knowledge of this should enable an appropriate scale of scrutiny to locate dust events effectively in the forward scattering signal. The diffusion constant of a 1 micron particle in water at 25 degrees is around 5 microns 2 per second; hence tens of seconds would be required for such an intrusive particle to remove itself from a batch scattering experiment and longer off times for the correlation process would be applied.

Figure 3:
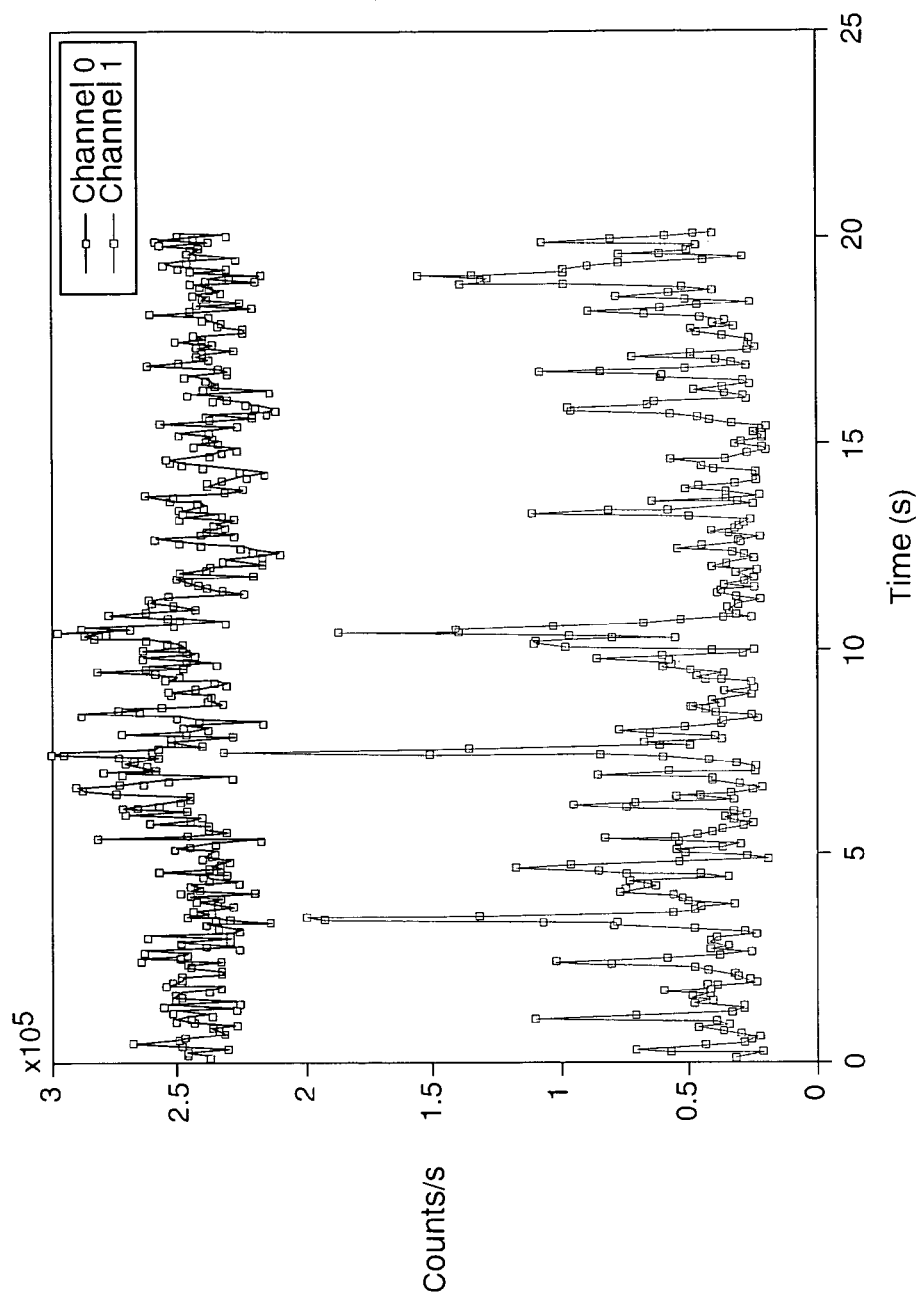
FIG. 3 is an illustrative timing diagram for a multi-detector light scattering apparatus according to the invention, such as the one shown in FIG. 1.

In FIG. 3, the count rate in the back scatter detector is labeled channel 0 while count rate in the forward scatter detector is labeled channel 1. The data was taken with detectors observing a 30 nm sample dispersed in water with some aggregates of micron size also present. The greater sensitivity of the forward detector to the contaminants is shown by the greater upward fluctuations in the signal where the maximum count rate to base level ratio reaches around 10:1, while the same ratio in the backward detector is around 1.3:1. One can also see that the count rate 'spikes' in the forward detector align in many cases (but not all) with smaller spikes in the backward case: however the great fluctuation in the forward detector is clearly resolved from the baseline and enables the data in the back scatter detector to be removed. This enables improved processing of the back scatter signal by eliminating the region where aggregates are contributing to the signal but not clearly detected as so-doing in the back channel alone.

Figure 4:
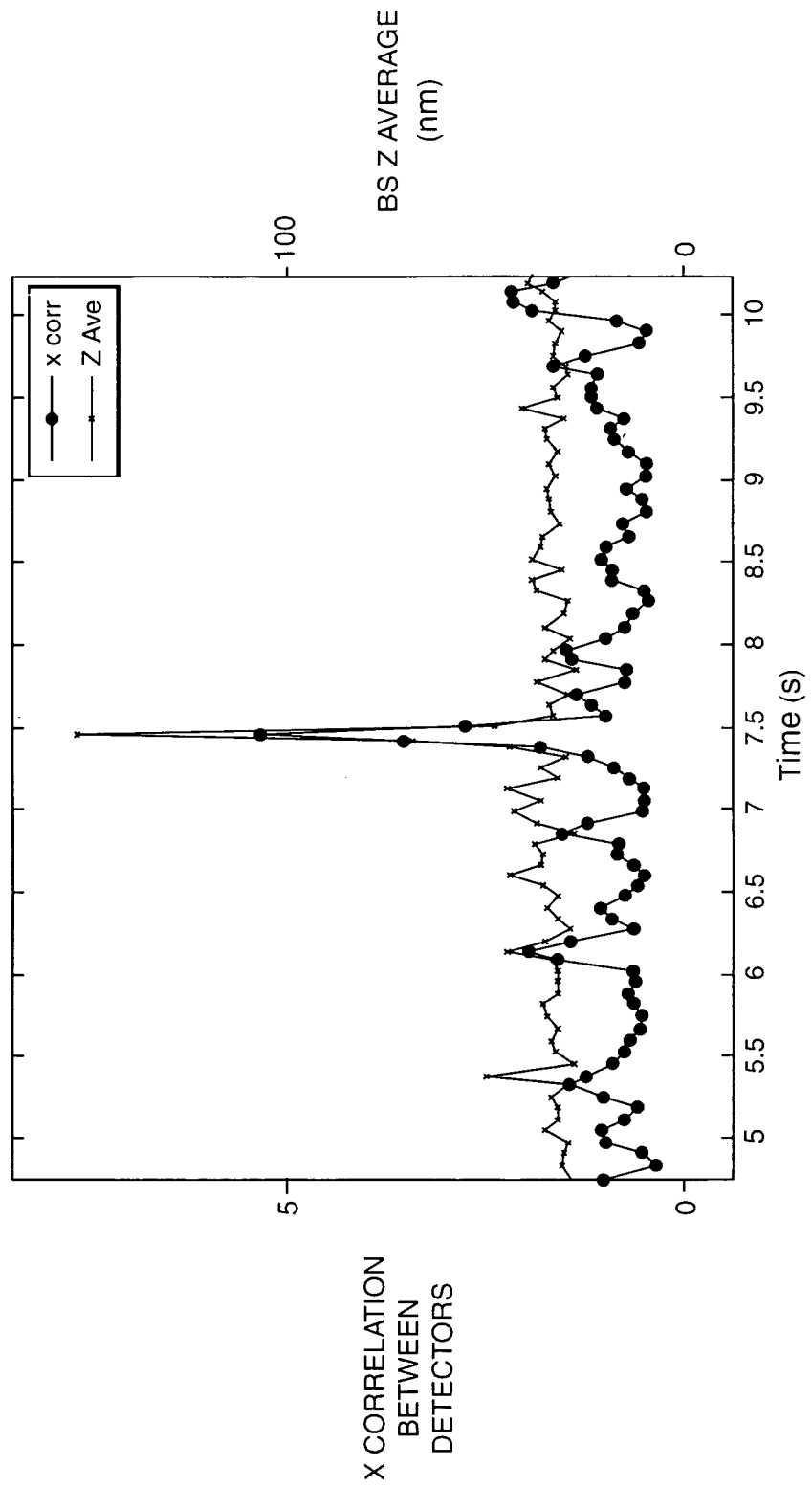
FIG. 4 is an illustrative cross correlation diagram for the same data set used for FIG. 3.

In FIG. 4, a processing scheme is shown in actual use. The plots are of 'x corr', a variant of the cross correlation function between the count rate signals in the two detectors and a particle size (Z Average) derived from the photon data in the back scatter detector alone. The data is from the same set as in FIG. 3: it is noted that near 7.5 seconds there is a sharp spike in the cross correlation which aligns with a sudden jump in the mean size, and by removing the underlying photon data during this spike improved size information can be gathered. It is also noted that this 'spike' covers around 120 ms during which the back scatter detector counted around 40,000 events. Smaller spikes are seen around 5.4 and 6 seconds.

The cross correlation function used in the illustration is $$C(T)=G(T)*H(T+t)/(<G>*<H>)$$

Where G is the counts in channel 0 and H in channel 1. The lag time 't' may be introduced if the events should be displaced in time, for example if the detectors were set to observe different regions of a flowing sample. In the case presented the detectors were observing the same region of the sample and t was set to 0.

The averaging, which is shown by the chevrons ("<", ">"), is taken over the time window of the experimental period, the function is calculated at each sample of the count rate which in the data presented was 50 ms. Other periods such as 1 ms can be used providing the sampling period represents many coherence times of the diffusion signal processed by the backscatter detector. Since all photon events from each detector are stored in real time they can be processed over different intervals for different purposes.

Figure 5:
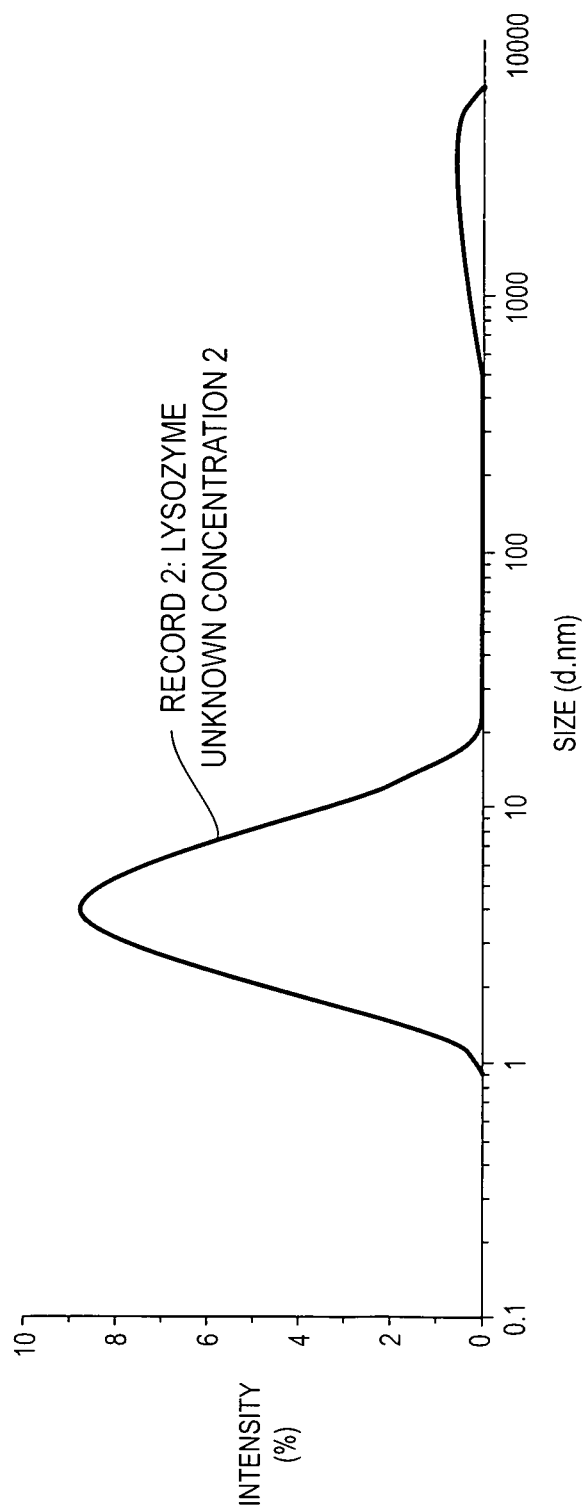
FIG. 5 is an illustrative plot of size against intensity obtained for a slightly aggregated sample of Lysozyme.
Figure 6:
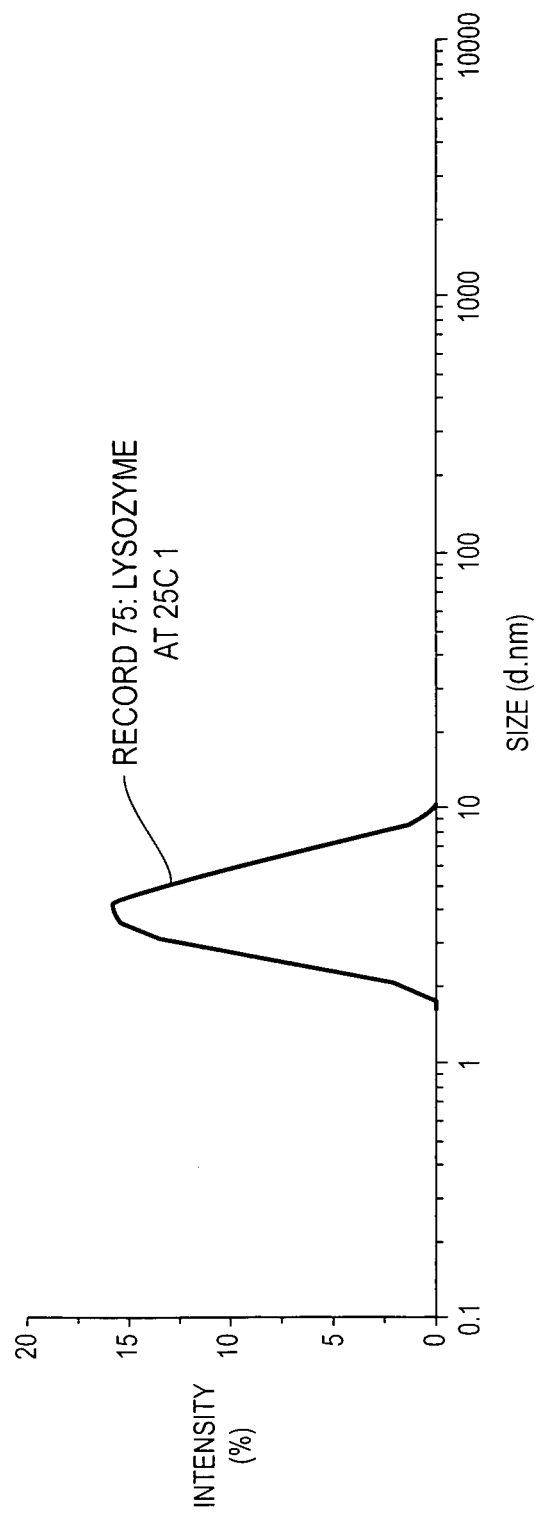
FIG. 6 is an illustrative plot of size against intensity obtained for a low concentration sample of Lysozyme.

FIG. 5 shows an illustrative plot of size against intensity obtained for a slightly aggregated sample of Lysozyme. In this plot, a second concentration peak caused by the presence of aggregates is apparent. In FIG. 6, a similar plot obtained for a low concentration sample of Lysozyme, the second peak is not visible, and the main peak is narrower. These two plots illustrate how the detection of particle characteristics, such as size, should improve when the effects of aggregates are mitigated.

The present invention has now been described in connection with a number of specific embodiments thereof. However, numerous modifications which are contemplated as falling within the scope of the present invention should now be apparent to those skilled in the art. While measurements in the visible wavelength range are currently contemplated, for example, it should also be possible to perform measurements at near-infrared or even ultraviolet wavelengths. It is therefore intended that the scope of the present invention be limited only by the scope of the claims appended hereto. In addition, the order of presentation of the claims should not be construed to limit the scope of any particular term in the claims.

What is claimed is:

1. A particle measurement instrument, comprising:
a light source having an output beam path,
a sample cell positioned in the output beam path of the light source,
at least one photon-counting detector positioned outside of the beam path to acquire light scattered along a first scattering angle,
a supplemental detector positioned outside of the beam path to acquire light scattered along a second scattering angle, different from the first, and
a processor comprising simultaneous detection logic responsive to both the photon-counting detector and the supplemental detector and having a particle characteristics measurement output, wherein the simultaneous detection logic includes inter-detector timing logic operative to derive the particle characteristics measurement output based at least in part on the timing between information from the photon-counting detector and information from the supplemental detector.

2. The instrument of claim 1 wherein the supplemental detector is also a photon-counting detector.

3. The instrument of claim 1 wherein the light source is a coherent visible light source.

4. The instrument of claim 1 wherein the light source is a narrowband visible light source.

5. The instrument of claim 1 wherein the simultaneous detection logic includes dynamic light scattering detection logic.

6. The instrument of claim 1 wherein the simultaneous detection logic operates in real time to allow information from the supplemental detector to gate information from the photon-counting detector.

7. The instrument of claim 1 wherein the simultaneous detection logic is operative to post-process acquired data from the photon-counting detector and acquired data from the supplemental detector after acquisition of the data from the photon-counting detector and the supplemental detector.

8. The instrument of claim 7 wherein the simultaneous detection logic includes digital signal processing logic.

9. The instrument of claim 7 wherein the simultaneous detection logic is interactive.

10. The instrument of claim 1 wherein the simultaneous detection logic is operative to determine the size of particles in the presence of larger contaminant particles.

11. The instrument of claim 1 wherein the simultaneous detection logic is operative to determine relative quantities of particles in the presence of larger contaminant particles.

12. The instrument of claim 1 wherein the supplemental detector is positioned from about 5-30 degrees off of an optical axis of the light source.

13. The instrument of claim 1 wherein the photon-counting detector is positioned about 7 degrees off of an optical axis of the light source.

14. The instrument of claim 1 further including a second photon-counting detector and wherein the simultaneous detector is further responsive to the second photon-counting detector.

15. The instrument of claim 14 wherein the second photon-counting detector is placed at about 90 degrees off of an optical axis of the light source at the sample cell.

16. The instrument of claim 1 wherein the instrument has a range of particle detection that covers particles that are smaller than 100 nm in diameter.

17. The instrument of claim 1 wherein the instrument has a range of particle detection that covers particles that are smaller than 10 nm in diameter.

18. The apparatus of claim 1 wherein the simultaneous detection logic includes cross-correlation logic operative to derive the particle characteristics measurement output based at least in part on a cross-correlation between information from the photon-counting detector and information from the supplemental detector.

19. The apparatus of claim 18 wherein the cross-correlation logic gates information from the photon-counting detector when a cross correlation between output of the photon-counting detector and the supplemental detector exceeds a predetermined threshold.

20. The instrument of claim 1 wherein the photon-counting detector is located on the same side of the sample cell as the light source and is positioned outside of the beam path to acquire backward scattered light, and wherein the supplemental detector is positioned opposite the light source from the sample cell to acquire forward scattered light.

21. The instrument of claim 1 wherein the supplemental detector is positioned from about 30-90 degrees off of an optical axis of the light source.

22. A method of measuring particle characteristics, comprising:
shining light on a suspended sample,
using a photon detector to acquire a photon count arising from scattering of the light by the sample,
using a supplemental detector to detect an amount of light arising from interaction between the light and the sample simultaneously with the step of acquiring a photon count, wherein the step of detecting detects a least some light from a direction different than a direction from which the photon count is acquired, and
using a processor to derive at least one measure of particle characteristics wherein the step of using a processor to derive is responsive to both the photon-counting detector and the supplemental detector and is operative to derive the particle characteristics measurement output based at least in part on the timing between information from the photon-counting detector and information from the supplemental detector.

23. The method of claim 22 wherein the step of shining light shines light on suspended biomolecules.

24. The method of claim 23 wherein the step of shining light shines light on suspended proteins.

25. A particle measurement instrument, comprising:
means for shining light on a suspended sample,
photon-counting detection means for acquiring a photon count arising from scattering of the light by the sample,
supplemental detection means for detecting an amount of light arising from interaction between the light and the sample simultaneously with an acquisition of a photon count, wherein the means for detecting detects a least some light from a direction different than a direction from which the photon count is acquired, and
processing means for deriving at least one measure of particle characteristics, wherein the means for deriving is responsive to both the photon-counting detection means and the supplemental detection means and is operative to derive the particle characteristics measurement based at least in part on the timing between information from the photon-counting detection means and information from the supplemental detector means.

* * * * *